United States Patent [19]

Hirano et al.

[11] Patent Number: 5,247,944
[45] Date of Patent: Sep. 28, 1993

[54] SKIN MOVEMENT DETECTOR

[75] Inventors: Shinichi Hirano; Yasuhiro Goto, both of Aichi, Japan

[73] Assignee: Kabushiki Kaisha Tokai Rika Denki Seisakusho, Aichi, Japan

[21] Appl. No.: 939,047

[22] Filed: Sep. 3, 1992

Related U.S. Application Data

[63] Continuation of Ser. No. 682,090, Apr. 9, 1991, abandoned.

[30] Foreign Application Priority Data

Apr. 10, 1990 [JP] Japan .................................. 2-38758

[51] Int. Cl.$^5$ ............................................ A61B 5/117
[52] U.S. Cl. ................................... 128/782; 128/687; 73/862.451
[58] Field of Search ............... 128/774, 782, 675, 672, 128/677, 687, 748, 721, 722, 689, 688, 775, 778; 73/862.451, 862.471, 862.473, 862.474, 862.541

[56] References Cited

U.S. PATENT DOCUMENTS

| | | | |
|---|---|---|---|
| 4,240,444 | 12/1980 | Virgulto et al. | 128/782 |
| 4,561,447 | 12/1985 | Kawamura et al. | 128/687 |
| 4,696,307 | 9/1987 | Montgieux | 128/721 |
| 4,920,972 | 5/1990 | Frank et al. | 128/675 |
| 4,976,272 | 12/1990 | Bazin et al. | 128/774 |
| 5,027,828 | 7/1991 | Kovacevic et al. | 128/774 |

FOREIGN PATENT DOCUMENTS

| | | | |
|---|---|---|---|
| 2609622 | 7/1988 | France | 128/689 |
| 927228 | 9/1976 | U.S.S.R. | 128/687 |
| 993915 | 3/1979 | U.S.S.R. | 128/687 |
| 1233861 | 1/1984 | U.S.S.R. | 128/687 |
| 1364293 | 12/1985 | U.S.S.R. | 128/672 |
| 1454378 | 1/1989 | U.S.S.R. | 128/689 |

*Primary Examiner*—Max Hindenburg
*Assistant Examiner*—Guy V. Tucker
*Attorney, Agent, or Firm*—Finnegan, Henderson, Farabow, Garrett & Dunner

[57] ABSTRACT

A skin movement detector is disclosed which comprises a case having an opening; a pressure-sensitive element having a diaphragm portion and disposed within the case; and a contact probe, made of a soft member, for contacting a skin surface, the contact probe being attached to the case so as to cover the opening and having a projecting portion contacting the diaphragm portion; the contact probe including a plate portion adapted to contact the skin, a base portion, and a leg portion connecting the plate portion and the base portion. The skin movement detector may also include regulating means positioned at an outer periphery of the projecting portion for contacting the diaphragm support portion peripherally when a force exceeding a predetermined value is applied to the contact probe. The skin movement detector thus provides high sensitivity in all directions across the skin and prevents excessive displacement of the diaphragm.

9 Claims, 2 Drawing Sheets

SKIN MOVEMENT DETECTOR

This application is a continuation of application Ser. No. 07/682,090, filed Apr. 9, 1991, now abandoned.

BACKGROUND OF THE INVENTION

The device relates to a skin movement detector which detects displacements on a skin surface using a pressure-sensitive element having a diaphragm.

Skin movement detectors detect the soundness of muscles governed by a nerve by causing a skin surface corresponding to the muscles to be moved by, e.g., electrically stimulating the nerve.

A conventional skin movement detector is shown in FIGS. 5 and 6. A pressure-sensitive element 52 is disposed at the inner bottom of a cylindrical case 51 which has an opening. A membrane 53 made of a soft material is attached to the case so as to cover the opening of the case 51 and contact a skin surface. At the periphery of the membrane 53 is a flange-like portion 54 extending outwardly from the case. On an inner surface of the membrane 54 is a projection 55 whose tip is formed integrally with the membrane and contacts the pressure-sensitive element 52.

According to this skin movement detector, the flange-like portion 54 is displaced by movement of the skin causing its base in contact with the case 51 to serve as a fulcrum. The displacement is transmitted to the projection 55 to change the biasing force applied from the projection to the pressure-sensitive element 52, thereby allowing skin movements to be detected.

In the above construction, the movement of the membrane 53 and thus the projection 55 is limited because a portion of at which the membrane is adhesively fixed to the case 51. As a result, the sensitivity of the membrane is undesireably impaired, particularly, in directions other than in the direction shown by arrow D in FIG. 5. Further, if projection 55 is moved too far in the direction shown by arrow D, the pressure-sensitive element 52 may be damaged.

SUMMARY OF THE INVENTION

The invention has been made in view of the above circumstances.

Accordingly, an object of the invention is to provide a skin movement detector with high sensitivity in all direction across the skin.

Another object of the invention is to provide a highly sensitive skin movement detector capable of preventing the displacement of the diaphragm of the pressure-sensitive element from exceeding an allowable range even in a large force were applied to the contact probe.

To achieve the above objects, a first embodiment of the invention comprises a skin movement detector which includes a pressure-sensitive element having a diaphragm on an inner surface of a case that has an opening. A silicone rubber contact probe is adhesively attached to the opening of the case. The contact probe has a projection extending from a base portion that covers the opening of the case. Extending from the middle of the base portion is a leg portion connected to a plate located external to the base portion.

A second embodiment of the invention, comprises a skin movement detector which includes a pressure-sensitive element having a diaphragm on an inner surface of a case that has an opening. A soft member contact probe is attached to the case covering the opening of the case. In such a skin movement detector, the contact probe includes a regulating section, which is positioned at an outer periphery of the projection and which contacts a peripheral portion of the diaphragam support when a force exceeding a predetermined value is applied to the contact probe.

According to the skin movement detector of the invention, upon transmission of movements to the contact probe, the movements of the projection cause the diaphragm to be displaced, thereby causing the pressure-sensitive element to detect the movements. Further, upon application of a force exceeding a predetermined value to the contact probe, the regulating section contacts the peripheral portion of the diaphragm support hence regulating excessive displacement of the diaphragm. As a result, the diaphragm is not subjected to displacement more than allowed, and the device has high sensitivity in all directions across the skin.

DESCRIPTION OF THE PREFERRED EMBODIMENTS

A first embodiment of the invention will be described with reference to FIG. 1.

Figure 1:
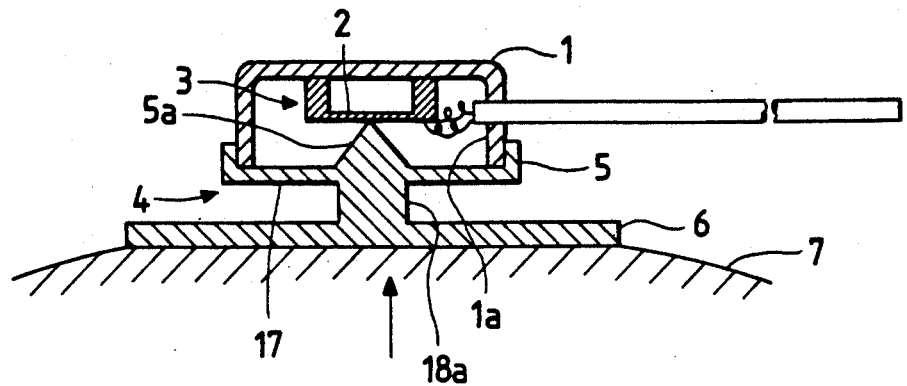
FIG. 1 is a longitudinal sectional view of a first embodiment of the present invention.

In FIG. 1, a pressure-sensitive element 3 having a diaphragm 2 is attached to an inner surface of a case 1. A silicone rubber contact probe 4 is adhesively attached to an opening 1a of the case 1. The contact probe 4 has a conical projection 5a and a base portion 5 that covers the opening 1a of the case 1. The contact probe 4 contacts the diaphragm 2. Extending from the middle of the base portion 5 is a leg portion 18a connected to a plate 6 located external to the base portion.

In this skin movement detector, the case 1 is fixed to the body of the person to be measured using tape so that the plate 6 comes in contact with a skin surface 7 of a measuring position. When muscles move and cause the skin surface 7 to move, the plate 6 which is in contact with the skin surface 7 receives a force exerted in a direction indicated by the arrow in FIGS. 1-4, causing the projection 5a to displace the diaphragm 2. This displacement is detected as an electric signal by the pressure-sensitive element 3 in the manner well known to those skilled in the art.

The above embodiment enjoys the following advantages. Since the base portion 5 communicates with the plate 6 through the leg portion 18a, the base portion is freely movable, thereby detecting the movements on the skin surface with high sensitivity.

A second embodiment of the invention will be described next with reference to FIGS. 2 to 4.

Figure 2:
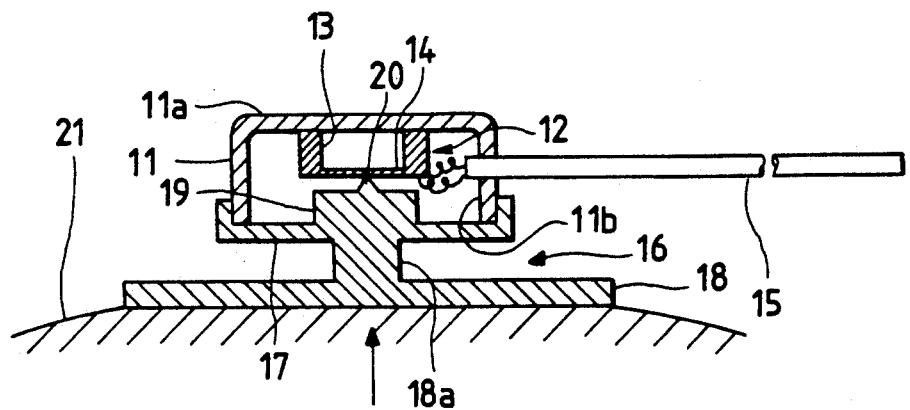
FIG. 2 is a longitudinal sectional view of a second embodiment of the present invention.

In FIG. 2, reference numeral 11 denotes a plastic case which has a short cylindrical form with an end 11a thereof closed. A pressure-sensitive element 12 is arranged within this case 11. The pressure-sensitive element 12 includes a diaphragm 14 and four strain gauge resistors (not shown) that are connected in the form of a bridge circuit. The resistors may be, for example diffusion resistors or thin film resistors. The diaphragm 14 is formed integrally with an end of a support 13, the other end of the support 13 being adhesively attached to the inner surface of the closed end 11a of the case 11. Signals detected by the strain gauge resistors are outputted by a signal line 15. Contact probe 16 is made of a soft member such as silicon rubber and is adhesively attached to the case 11 so that a base portion 17 thereof closes an opening 11b of the case 11. Extending from the middle of the base portion 17 is a leg portion 18a connected to a plate 18 located external to the base portion. Further, internal to the base portion 17 is a cylindrical regulating section 19 arranged integrally with the base portion 17 in the middle thereof. The regulating section 19 includes a conical projection 20 formed integrally with the regulating section 19 in the middle thereof. The tip of the projection 20 contacts the middle portion of the diaphragm 14. In this case, the outer diameter of the regulating section 19 is defined so as to be at least larger than the inner diameter of the support 13, while the projecting dimension of the projection 20 is set to a value substantially equal to that of the tip of the projection 5a in the first embodiment.

In the above construction, the case 11 is fixed with a tape so that the plate 18 comes in contact with a skin surface 21 of a measuring position. When muscles move and cause the skin surface 21 to move, the plate 18 which is in contact with the skin surface 21 receives a force exerted in a direction indicated by the arrow, subjecting the base portion 17 to elastic deformation, which then causes the projection 20 to compress the diaphragm 2. This causes resistances of the stain gauges arranged on the diaphragm 14 to be changed, and this change is detected as an electric signal and outputted by the signal line 15.

Figure 3:
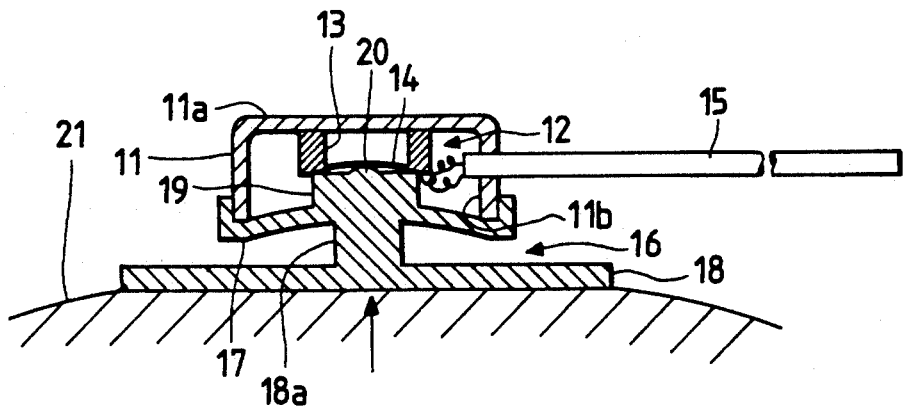
FIG. 3 is a longitudinal sectional view of the second embodiment of the present invention in an activated state.
Figure 4:
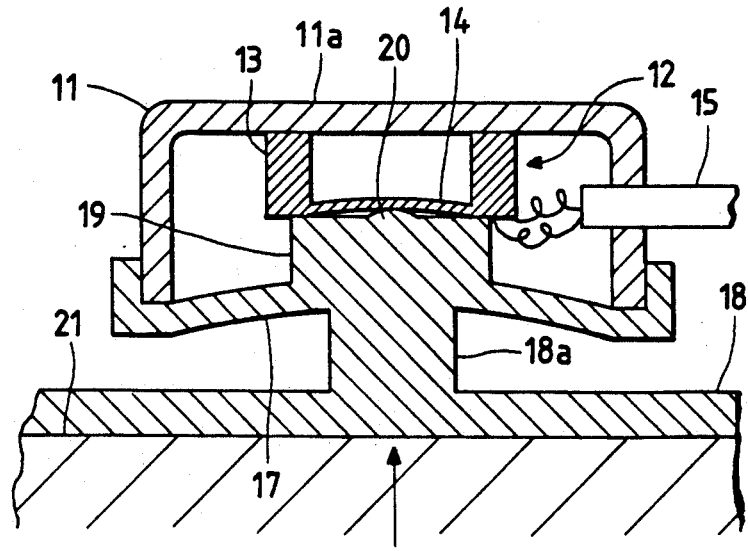
FIG. 4 is a longitudinal sectional view showing a main portion of the second embodiment in an adviated state.
Figure 5:
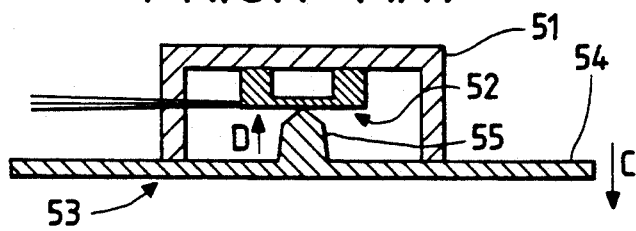
FIG. 5 is a longitudinal sectional view showing a conventional skin movement detector.
Figure 6:
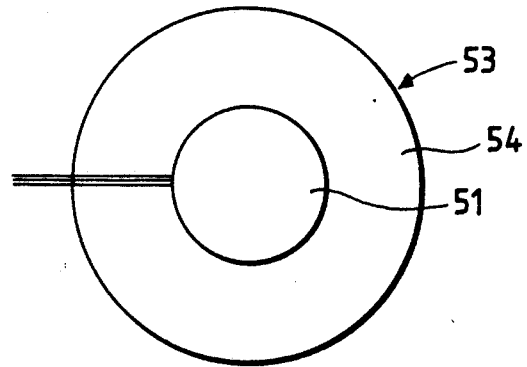
FIG. 6 is a plan view showing the conventional skin movement detector.

As shown in FIGS. 3 and 4, when a force larger than a predetermined is applied to the plate 18 in the direction indicated by the arrow, the base portion 17 of the contact probe 16 deforms elastically more than usual, thereby causing the projection 20 to bias the diaphragm 14 in the direction indicated by the arrow. In this case, the displacement of the diaphragm 14 is larger than usual, causing much of the projection 20 to be elastically collapsed. Accordingly, the upper surface of the regulating section 19 contacts the lower surface of the support 13, checking the movement of the projection 20. As a result, the diaphragm 14 is no longer deformed by the projection 20. When the force applied to the plate 18 in the direction indicated by the arrow is removed, the projection 20 elastically returns so as to be capable of projecting upward.

According to the above embodiments, the following advantages are provided. The contact probe 16 has the regulating section 19 that may contact the outer periphery of the projection 20 so that when the contact probe 16 receives a force exceeding a predetermined value, the regulating section 19 is caused to contact the support 13 peripherally supporting the diaphragm 14. As a result, the diaphragm 14 is not displaced further, thereby preventing the diaphragm from displacing more than allowed damaging the diaphragm or strain gauges.

The skin movement detector of the invention, in which the base portion is attached to the plate through the leg portion, allows the base portion to be freely movable, thereby detecting movements of a skin surface with high sensitivity. Further, the skin movement detector is provided with the regulating section, which contacts the support peripherally supporting the diaphragm when an excessive force is applied to the contact probe and projection that contacts the diaphragm of the pressure-sensitive element. This prevents the diaphragm of the pressure-sensitive element from being displaced more than allowed.

We claim:

1. A skin movement detector comprising:
   a case having an opening;
   a pressure-sensitive element having a diaphragm portion and disposed within said case; and
   a contact probe, made of a flexible member, for contacting a skin surface, said contact probe being attached to said case so as to cover said opening and having a projecting portion contacting said diaphragm portion;
   said contact probe including a plate portion adapted to contact the skin, a base portion covering said opening, and a leg portion connecting and integral with said plate portion and said base portion, wherein movement of the skin surface is transmitted from said plate portion to said projecting portion to displace said diaphragm portion, said pressure-sensitive element detecting the displacement of the diaphragm portion as an indication of the skin movement.

2. The detector of claim 1, wherein said plate portion is disc-shaped.

3. The detector of claim 1, wherein said projecting portion is cone-shaped.

4. A skin movement detector comprising:
   a case having an opening;
   a pressure-sensitive element disposed within said case and having a diaphragm portion and a support portion connecting said diaphragm portion to said case; and
   a contact probe, made of a flexible member, for contacting a skin surface, said contact probe being attached to said case so as to cover said opening;
   said contact probe including a regulating means defining a distal end extending toward said pressure-sensitive element and a projecting portion extending from said distal end and contacting said diaphragm portion, said regulating means contacting said support portion when a force exceeding a predetermined value is applied to said contact probe, wherein movement of the skin surface is transmitted to said projecting portion to displace said diaphragm portion, said pressure-sensitive element detecting the displacement of said diaphragm portion as an indication of the skin movement.

5. The detector of claim 4, wherein said contact probe includes a plate portion adapted to contact the skin, a base portion covering said opening, and a leg portion connecting and integral with said plate portion and said base portion.

6. The detector of claim 5, wherein said support portion comprises an annulus defining a longitudinal axis and said regulating means comprises a cylinder having a longitudinal axis coaxial with said annulus longitudinal axis, an outer diameter of said regulating means being larger than an inner diameter of said support portion.

7. The detector of claim 6, wherein said projecting portion is cone-shaped.

8. The detector of claim 5, wherein said plate portion is disc-shaped.

9. The detector of claim 4, wherein said projecting portion is cone-shaped.

* * * * *